United States Patent
Takasawa

(10) Patent No.: US 8,121,257 B2
(45) Date of Patent: Feb. 21, 2012

(54) X-RAY IMAGE CAPTURING DEVICE AND A METHOD THEREOF

(75) Inventor: Toru Takasawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 99 days.

(21) Appl. No.: 12/617,155

(22) Filed: Nov. 12, 2009

(65) Prior Publication Data
US 2010/0150311 A1   Jun. 17, 2010

(30) Foreign Application Priority Data

Dec. 11, 2008   (JP) .................................. 2008-316273

(51) Int. Cl.
*H05G 1/56* (2006.01)
(52) U.S. Cl. ......................................... 378/115; 378/62
(58) Field of Classification Search ............... 378/62, 378/98, 98.2, 115, 117, 204
See application file for complete search history.

(56) References Cited

U.S. PATENT DOCUMENTS
2007/0253531 A1* 11/2007 Okuzawa et al. ............... 378/62

FOREIGN PATENT DOCUMENTS
JP   2000-308631   11/2000
JP   2006-007190   1/2006

* cited by examiner

*Primary Examiner* — Hoon Song
(74) *Attorney, Agent, or Firm* — Fitzpatrick, Cella, Harper & Scinto

(57) ABSTRACT

In an X-ray image capturing device which performs image capturing by receiving image capturing information that includes protocols from an information system, when a protocol which is not associated to a body part is transferred, image capturing of such protocol cannot be performed, or the task of associating it to a body part is troublesome and may not be performed accurately. A configuration is used in which a protocol having unassociated image capturing information and body part is displayed as an undefined protocol, and means to associate the undefined protocol to a body part is called up.

12 Claims, 15 Drawing Sheets

F I G. 4
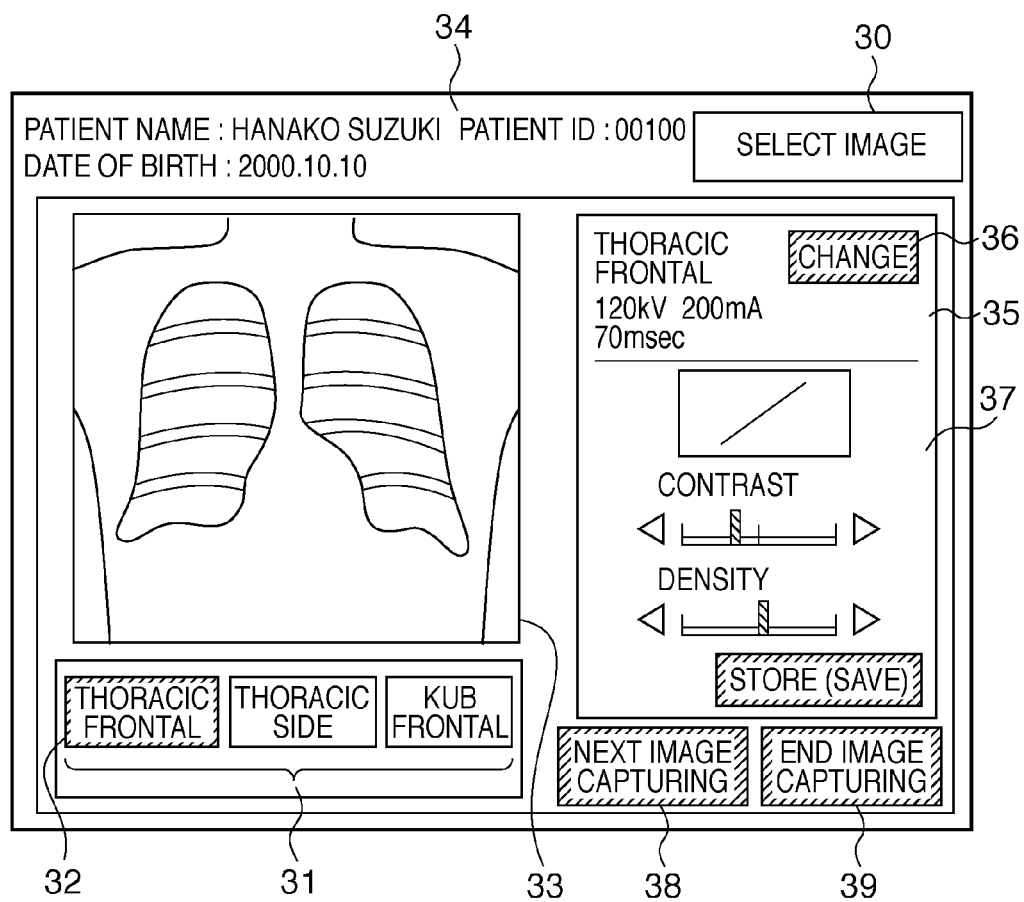

FIG. 5

| PROTOCOL ID | PROTOCOL NAME | kV | mA | mS | cm |
|---|---|---|---|---|---|
| 100200120 | THORACIC P-A (STANDING) | 110 | 320 | P | 200 |
| 100201120 | THORACIC P-A (SEATED) | 110 | 320 | P | 200 |
| 100200110 | THORACIC A-P (STANDING) | 110 | 320 | P | 200 |
| 100201110 | THORACIC A-P (SEATED) | 110 | 320 | P | 200 |
| 100200130 | THORACIC R-L (STANDING) | 120 | 630 | P | 200 |
| ... | ... | ... | ... | ... | ... |
| 100200180 | THORACIC LAO (STANDING) | 110 | 500 | P | 200 |
| ... | ... | ... | ... | ... | ... |
| 100800120 | ABDOMINAL P-A (STANDING) | ... | ... | ... | ... |
| 100800130 | ABDOMINAL R-L (STANDING) | ... | ... | ... | ... |
| ... | ... | ... | ... | ... | ... |
| 100800110 | KUB P-A (STANDING) | ... | ... | ... | ... |
| ... | ... | ... | ... | ... | ... |

FIG. 6

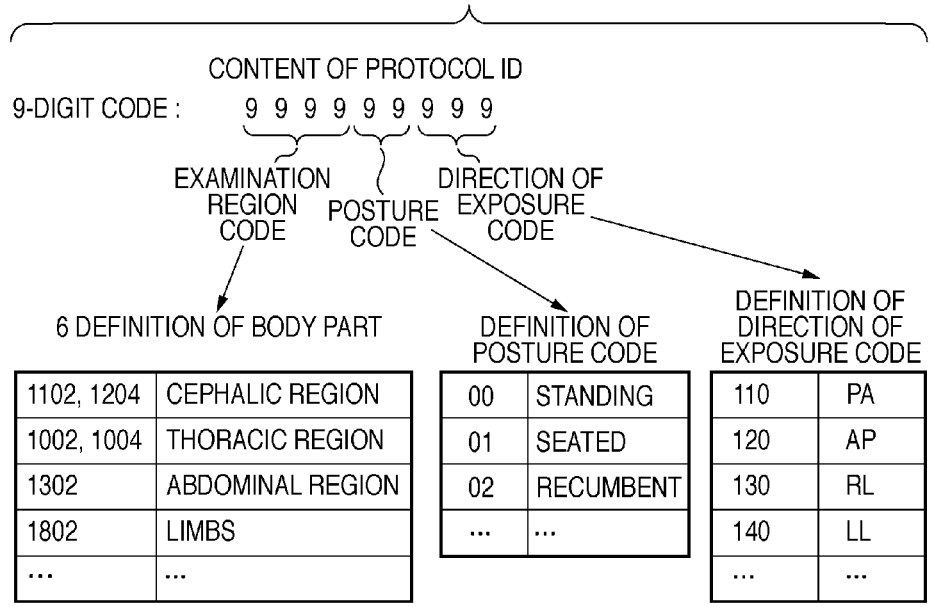

CONTENT OF PROTOCOL ID
9-DIGIT CODE: 9 9 9 9 9 9 9 9 9

EXAMINATION REGION CODE
POSTURE CODE
DIRECTION OF EXPOSURE CODE

6 DEFINITION OF BODY PART

| 1102, 1204 | CEPHALIC REGION |
| 1002, 1004 | THORACIC REGION |
| 1302 | ABDOMINAL REGION |
| 1802 | LIMBS |
| ... | ... |

DEFINITION OF POSTURE CODE

| 00 | STANDING |
| 01 | SEATED |
| 02 | RECUMBENT |
| ... | ... |

DEFINITION OF DIRECTION OF EXPOSURE CODE

| 110 | PA |
| 120 | AP |
| 130 | RL |
| 140 | LL |
| ... | ... |

FIG. 7

| BODY PART CODE | BODY PART NAME (BUTTON NAME) | PROTOCOL ID |
|---|---|---|
| 100 | THORACIC FRONTAL | 100200120, 100201120 |
| 101 | PULMONARY APEX | 100200121 |
| 102 | THORACIC OBLIQUE | 100200122 |
| 103 | THORACIC (RECUMBENT) | 100200123 |
| ... | ... | ... |
| 120 | THORACIC SIDE | 100200130 |
| ... | ... | ... |
| 130 | ABDOMINAL P-A (STANDING) | ... |
| 131 | ABDOMINAL R-L (STANDING) | ... |
| ... | ... | ... |
| 150 | KUB FRONTAL | ... |
| ... | ... | ... |

FIG. 8

| BODY PART CODE | BODY PART CODE NAME (BUTTON NAME) | IMAGE CAPTURING CONDITION | ANALYSIS FUNCTION | IMAGE PROCESSING PARAMETER | OUTPUT FORMAT |
|---|---|---|---|---|---|
| 100 | THORACIC FRONTAL | 110 | 320 | B10C20 | P2x2 |
| 101 | ... | ... | ... | ... | ... |
| 102 | THORACIC SIDE | 110 | 320 | B12C18 | P |
| 103 | ... | ... | ... | ... | ... |
| 104 | ... | ... | ... | ... | ... |
| ... | ... | ... | ... | ... | ... |
| 120 | THORACIC LAO (STANDING) | 110 | 500 | B10C15 | ... |
| ... | ... | ... | ... | ... | ... |
| 130 | ABDOMINAL P-A (STANDING) | ... | ... | ... | ... |
| 131 | ABDOMINAL R-L (STANDING) | ... | ... | ... | ... |
| ... | ... | ... | ... | ... | ... |
| 200 | KUB FRONTAL | ... | ... | ... | ... |
| ... | ... | ... | ... | ... | ... |

FIG. 9

| PATIENT INFORMATION | | | | IMAGE CAPTURING INFORMATION | | | |
|---|---|---|---|---|---|---|---|
| 000100 | HANAKO SUZUKI | F | 2000.10.10 | 100200120 | THORACIC P-A (STANDING) | 100200130 | THORACIC R-L (STANDING) | 130200110 | KUB A-P (STANDING) |

X-RAY IMAGE CAPTURING DEVICE AND A METHOD THEREOF

BACKGROUND OF THE INVENTION

1. Field of the Invention

The present invention relates to an X-ray image capturing device and a method of using that device.

2. Description of the Related Art

In recent years, an increasing number of X-ray image capturing devices intended for use in medical work utilize methods of digitally detecting and generating an X-ray image instead of using an X-ray photograph method which utilizes a combination of sensitizing sheets and films in the X-ray detection unit. As a well-known method of such, there is an X-ray image acquisition method which uses a flat panel sensor in the detection device. This type of method includes a method that utilizes a solid-state image sensor which is sensitive to X-rays, and a method that utilizes a combination of a fluorescent body which converts energy of X-rays into visible light and a photoelectric conversion element which is sensitive to visible light.

In the former method, the solid-state image sensor generates an output which is converted from detected X-rays in accordance with the intensity of the detected X-rays. For the latter method, fluorescence having an intensity in accordance to the energy of the X-rays is generated, and the fluorescence is converted to an electric signal by a photoelectric conversion element according to the intensity of the detected fluorescence. Subsequently, the analog signal generated by the photoelectric conversion element is digitalized by A/D conversion and is processed.

These digital X-ray image capturing devices are comprised of an inspection module which includes a detection device that detects a quantity of electricity which corresponds to the dose of X-rays that have passed through the patient and converts that quantity to a digital amount, and a controller which controls the detection module and an X-ray generating device. A radiologic technologist inputs patient information and sets various parameters in accordance with the body part concerned, after setting the patient in the standard position, and generates an X-ray image at the examination module by performing irradiation of the patient with X-rays.

The various parameters mentioned here include tube current, tube voltage, X-ray irradiation period, image capturing conditions such as size of aperture, and image processing parameters to be performed on the obtained images, and these parameters are set together when the body part is designated. Generated X-ray images are taken into the controller where various kinds of correction processing and image processing are performed, resulting in generation of digital X-ray images for use in diagnosis by physicians. These digital images can be output as required from a printer as films. Further, these digital images are sent to a storage, and then displayed on a monitor for use in diagnosis.

Recently, it has become rare for radiologic technologists to perform manual input of patient information and body parts into an X-ray image capturing system. It is becoming common to input patient information and body parts into digital X-ray image capturing devices via terminals of networks which are established in hospitals. Examples of such networks include the Hospital Information System (HIS) and the Radiology Information System (RIS).

As discussed in Japanese Patent Laid-Open No. 2000-308631 and Japanese Patent Laid-Open No. 2007-007190, a radiologic technologist adjusts in advance various types of parameters which correspond to an image capturing protocol (referred to as simply a "protocol" hereinafter) for capturing images ordered by HIS and/or RIS. The preset parameters are registered according to body part in the digital X-ray image capturing device. Further, association of the protocols ordered from HIS and RIS with the body part is performed. By doing so, a corresponding body part is easily selected when a protocol is sent from HIS or RIS, and various parameters preset for that body part are set, enabling the desired image capturing.

However, protocols ordered by HIS and/or RIS differ in type from one facility to another. Further, there can be generally more than 100 different combinations of region, direction and position. Further, to these combinations additional detailed classifications such as image capturing method and infant (not adult), often making raising the number of possible combinations to more than 200. Accordingly, presetting of various parameters in an X-ray image capturing device for these protocols becomes necessary. However, not all protocols are used with the same frequency in reality, and some protocols are actually never used.

For such reason, generally, the parameters only for major protocols are created as sets and are associated with the relevant body parts. However, when protocols that have not been associated are ordered by HIS or RIS, image capturing using these protocols cannot be performed.

Further, when associating a protocol with a body part, one had to take note of IDs of protocols which have not been associated, terminate the image capturing operation, and arrest image capturing flow. Subsequently, after terminating image capturing, a body part edit screen for service had to be called up in order to associate the protocol ID corresponding to the body part. Thus, the operation for association is troublesome, and also may cause erroneous setting because of its manual nature. Further, using the displayed protocol ID alone does not allow one to know easily which body part should be selected.

The present invention provides X-ray image capturing equipment which enables easy setting of the body part for protocols that are not associated with any body part, without stopping the image capturing flow.

SUMMARY OF THE INVENTION

In order to resolve the above problems, an X-ray image capturing device comprises a register unit for registering a body part and parameters related to capturing an image of the region, an order receiving unit which acquires an image capturing order, an associating unit for associating the image capturing information included in the image capturing order which indicates image capturing to be performed with the body part registered in the register unit, a display unit for displaying undefined image capturing information that could not be associated with a body part by the associating unit, and a selecting unit for displaying the body parts registered in the registered unit as candidates for the undefined image capturing information, and associating a body part selected by a user from the candidates to the undefined image capturing information. X-ray image capturing is performed using the body part associated with the image capturing information by the associating unit and the selecting unit and the parameters related to capturing an image of the region.

A first aspect of the present invention is simultaneously to display an undefined protocol ID with its image capturing information when no association is made between image capturing information and body part, making it possible to select the corresponding body part correctly.

A second aspect of the present invention is to display that a body part is undefined when the body part is not associated with image capturing information, and to set unset portions of a display region, enabling correct association by simple operation without stopping image capturing flow.

Further features of the present invention will become apparent from the following description of exemplary embodiments with reference to the attached drawings.

BRIEF DESCRIPTION OF THE DRAWINGS

FIG. 4 shows a GUI (confirmation of screen) displayed on the operation display unit of embodiment 1.

FIG. 5 shows an association table of protocol ID, protocol names and image capturing conditions.

FIG. 6 shows an example of content of protocol ID.

FIG. 7 shows an association table of body part name and protocols.

FIG. 8 shows an association table of content of body parts, body part names, image capturing conditions, etc.

FIG. 9 shows an example of image capturing order of embodiment 1.

DESCRIPTION OF THE EMBODIMENTS

Embodiments of the present invention will be explained below in detail based on attached figures.

Embodiment 1

Figure 1:
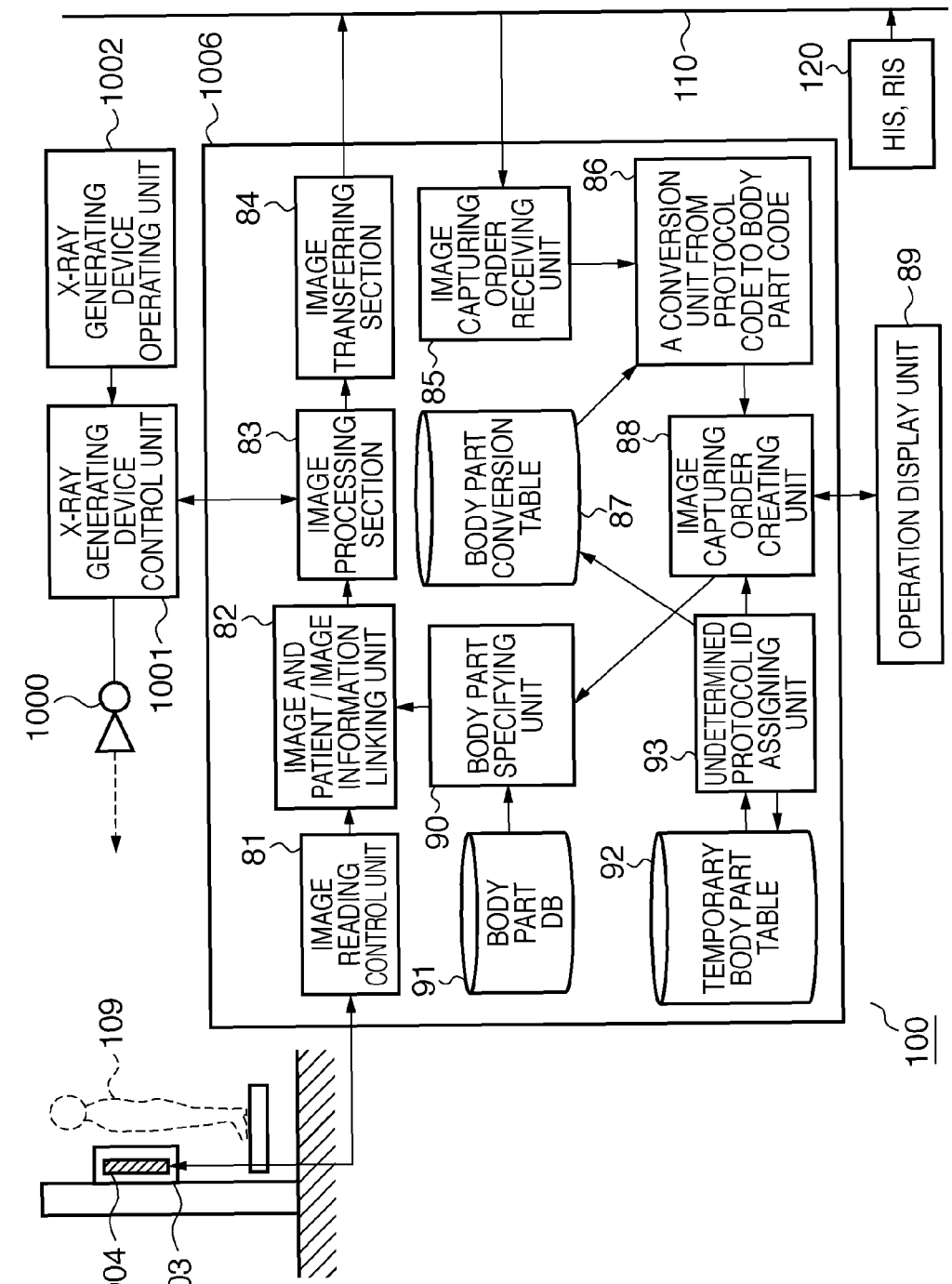
FIG. 1 is a block diagram showing an X-ray image capturing system according to embodiment 1.

FIG. 1 is a block diagram showing an X-ray image capturing system according to embodiment 1.

This X-ray image capturing system 100 comprises an X-ray tube bulb 1000, an X-ray generating device control unit 1001, an X-ray generating device operating unit 1002, an image capturing unit 1003, and an X-ray image capturing system control unit 1006.

The X-ray tube bulb 1000 generates X-rays. The X-ray generating device control unit 1001 causes the X-ray tube bulb 1000 to generate X-rays and controls the amount of X-rays to be irradiated. Further, the X-ray generating device operating unit 1002 is an operational station at which the radiologic technologist manually operates the X-ray generating device control unit 1001. Further, the image capturing unit 1003 detects X-rays emitted from the X-ray tube bulb 1000.

The control unit 1006 reads digital image signals obtained from/at the image capturing unit 1003, performs certain image processing, and then performs image display, image output, and control of the X-ray generating device. Further, the X-ray generating device control unit 1001 applies a high electric voltage to the X-ray tube bulb 1000 according to the image capturing conditions sent from the X-ray generating device operating unit 1002 or the control unit 1006, such as tube current, tube voltage and irradiation period, and leads to generation of the X-rays.

The image capturing unit 1003 comprises an X-ray detector 1004 for obtaining a digital image by detecting the X-rays irradiated from the X-ray tube bulb 1000, and an A/D converter for outputting the output of the X-ray detector 1004 as a digital image signal. Further, the image capturing unit 1003 can also additionally include an AEC (Auto-Exposure Control) device (not shown in the figure) which appropriately irradiates the amount of radiation that is required by the image capturing device while reducing the dose to the human body to a minimum, and a grid (not shown in the figure) for eliminating scattered X-rays.

The X-ray detector 1004 is comprised of a solid-state image sensor which generates electric signals that corresponds to a scintillator which converts X-rays to light and to light intensity.

The X-rays that have been irradiated into the image capturing unit 1003 from the X-ray tube bulb 1000 are separated from scattered X-rays which have been generated at a patient 109 at the grid. Subsequently, the X-rays that have passed through the grid are converted to light by the scintillator, and an electric signal is generated at the solid-state image sensor according to the light intensity. By passing this electric signal through the A/D converter, a digital X-ray image can be obtained.

The AEC device is placed between the grid and the X-ray detector 1004, and detects in real time the portion of radiation which has passed through the patient 109 and the grid, and transfers the generated AEC signal to the X-ray generating device controlling unit 1001. If the integrated value of the AEC signal exceeds a threshold value, the X-ray generating device control unit 1001 turns off the radiation generating signal, and stops generation of radiation from the X-ray tube bulb 1000. By doing so, the AEC device controls the irradiation amount appropriately.

The control unit 1006 of the X-ray image capturing system 100 can be roughly divided into two processing units, which are an image processing unit and an image capturing management unit. The image processing unit is comprised of an image reading control unit 81, an image and patient/image information linking unit 82, an image reading control unit 81, and an image transferring section 84. The image reading control unit 81 obtains digital X-ray image signals from the image capturing unit 1003, performs various types of correction processing such as gain correction and shading correction, and generates original images which become the bases of diagnostic images.

The image and patient/image information linking unit 82 performs association between original images, image information provided by a body part specifying unit 90, and patient information provided by a patient information notifying unit (not shown in the figure).

The image processing section 83 uses the image processing parameters which are a part of the associated image information, performs various types of processing such as a half-tone process, sharpening process and dynamic range compression, to the original image and generates a diagnostic image, and displays the diagnostic image on the operation display unit 89. Further, the image processing section 83 performs processing using a body part conversion table 87, a body part DB 91 and a temporary body part table 92.

Data of the body parts are made of two kinds of databases. In other words, one is a first database which corresponds to the body part DB 91, which stores body part data to be associated with identification (ID) of image-capturing information. The other is a second database which corresponds to the temporary body part table 92 that stores candidate data of body parts and their image-capturing conditions when conversion of body part by a conversion unit 86 from the protocol code cannot be done. In this example, the first database is made of a nonvolatile storage medium which preserves storage even when power is turned off, and the second database is made of a temporary storage medium which preserves storage only when the power is on. The image transferring section 84 transfers created diagnostic images to the network 110.

The image capturing management unit is made of an image capturing order receiving unit 85, a conversion unit 86 from protocol code to body part code, an image capturing order creating unit 88, a body part specifying unit 90, and an undefined protocol ID assigning unit 93.

The image capturing order receiving unit 85 receives patient information and image capturing order sent via the network 110 from HIS/RIS 120. The protocol ID of image capturing information included in the received image capturing order is converted from a protocol code to a corresponding body part code by the conversion unit 86. At this point, the protocol ID is a piece of definition information which identifies the type of image capturing. Further, by arranging the body part codes converted by the image capturing order creating unit 88 in sequence and displaying the orders, image capturing orders at the X-ray image capturing system 100 are determined.

The undefined protocol assigning unit 93, performs processing when the protocol ID included in the image capturing information received at the image capturing order receiving unit 85 is not associated with a body part code. In such cases, association of undefined protocol IDs and body part codes is performed, which are stored at the temporary body part table as well as at the body part DB 91, the latter being stored after confirmation by the operator.

The body part specifying unit 90, in accordance with the sequence of the image capturing orders created by the image capturing order creating unit 88, selects a body part and retrieves preset values for various types of parameters, and at the same time forwards the body part information to the image and patient/image information linking unit 82 sequentially.

The operation display unit 89 is a monitor for displaying instruction to perform operation of the X-ray image capturing device and/or image capturing, image processing for captured images, captured images, image capturing orders, messages, or status of devices. The operation display unit 89 is comprised of, for example, a liquid crystal panel, a touch sensor and a mouse.

Figure 2:
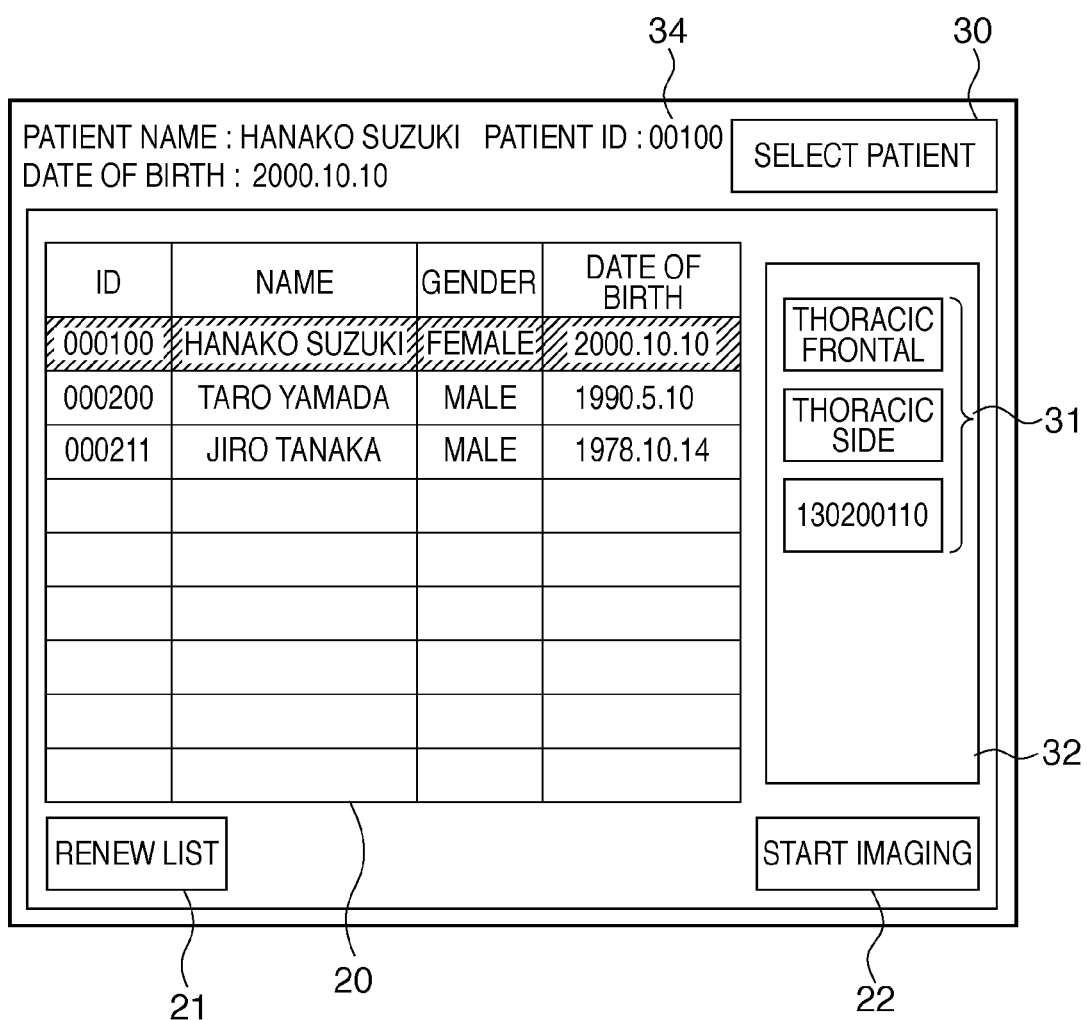
FIG. 2 shows a GUI (selection of patient) displayed on an operation display unit of embodiment 1.
Figure 3:
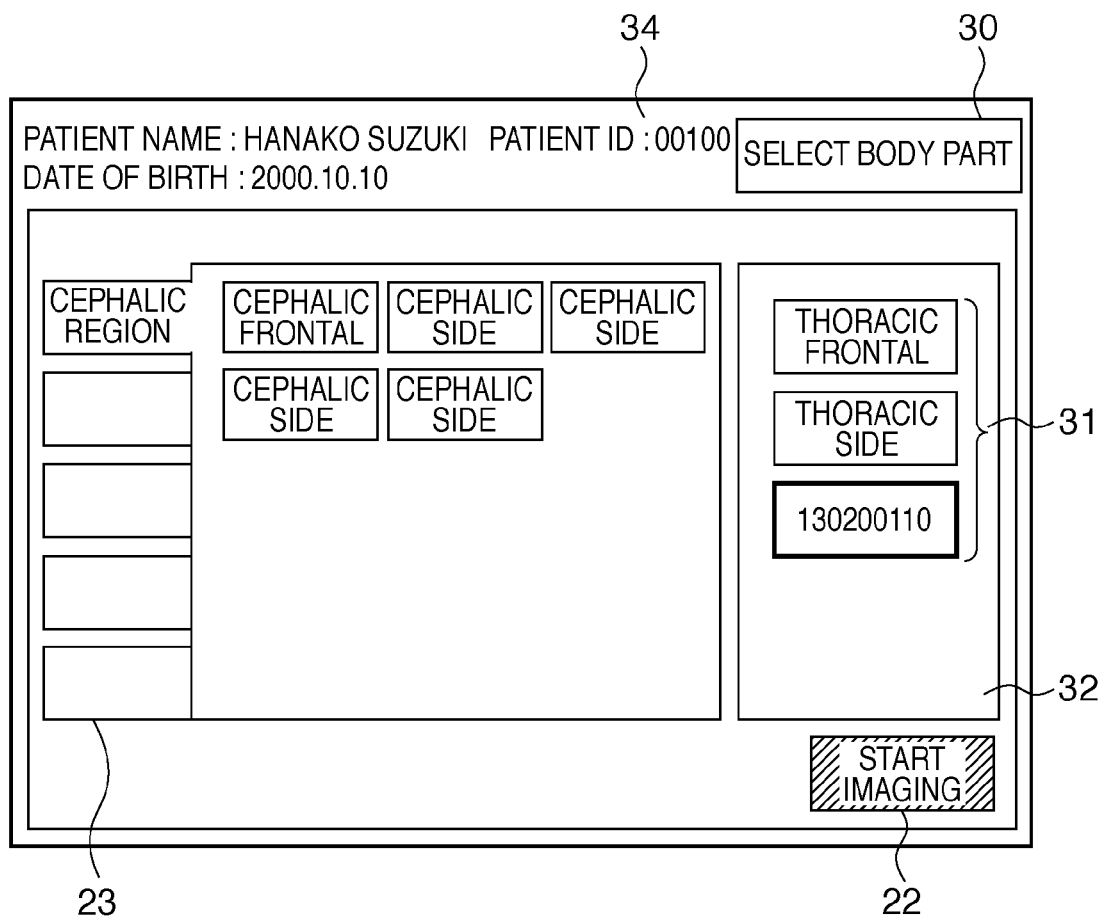
FIG. 3 shows a GUI (selection of body part) displayed on the operation display unit of embodiment 1.

FIGS. 2, 3 and 4 are diagrams showing examples of screens displayed on the operation display unit 89.

FIG. 2 shows a patient list selection screen for selecting image capturing orders of patients sent from the HIS/RIS 120 via the network 110.

FIG. 3 shows a screen which is used when there is a protocol ID that is not associated with a body part. In FIG. 3, association of undefined protocol ID is performed.

FIG. 4 shows a screen when X-ray irradiation is finished and a diagnostic image is displayed.

The patient list selection screen of FIG. 2 is comprised of a message/status display region 30, a body part-button displaying region 31, an image capturing order displaying region 32, a patient information displaying region 34, an image capturing order list 20, a list renewing button 21, an image capturing start button 22, and a patient information displaying region 34.

The patient information sent from the HIS/RIS 120 via the network 110 is acquired by the image capturing order receiving unit, and is displayed on the image capturing order list 20 in FIG. 2. This image capturing information includes ID distinguishing the type of image capturing and information regarding type of image capturing.

It is shown on the status display region 30 that the process is at a step of selecting a patient. When a certain patient from the image capturing order list 20 is selected, the image capturing order of the patient is recognized and displayed on the image capturing order display region 32. In this case, as shown in the display region 31, the image capturing orders are for a frontal thoracic image capturing, a side thoracic image capturing, and an image capturing by an undefined protocol.

On the screen of FIG. 3, which performs association of the undefined protocol ID and the body part, a body part menu 23 is a menu for use in selecting a body part from a plurality of body part candidates. On the status display unit 30, it is shown that the process is at a stage of selecting a body part. The protocol IDs, the body parts and its image capturing conditions are associated by selecting a button indicating an image capturing condition such as "cephalic frontal" or "cephalic side" at the same time as a button showing an undefined protocol ID which is displayed in a step below the display region 31.

In the image capturing screen of FIG. 4, an image displaying region 33 shows a region displaying the captured image, and a body part information display region 35 shows a region displaying information of the body part. It is shown in the status displaying region 30 that the process is currently at a step of checking the image. Further, this screen comprises a body part information changing button 36 which calls up a menu for changing information regarding body part, a subsequent image capturing button 38, and an image capturing end button 39. When performing a subsequent round of image capturing, the subsequent image capturing button 38 is pressed. When image capturing is to end, the image capturing end button 39 is pressed.

FIG. 5 shows an example of protocol content transferred from the RIS. Generally, this table is decided between the chief technologist and the technician of the RIS manufacturer after discussion. Protocol IDs and protocol names are associated with each other. For example, in the case of thoracic P-A (posteroanterior exposure), the protocol ID is "1002000120". This table also contains voltage, current, time, and distance of exposure as parameters.

FIG. 6 shows an example of a protocol ID. The protocol ID described here is shown as a 9-digit code. Each code is divided as shown in the figure, and is comprised of an examination region code, posture code and direction of exposure code. Each code has a definition file as shown in the respective tables.

FIG. 7 shows an example of the body part conversion table 87 of FIG. 1. Here, a table is shown in which the correspondence of the body part code, the body part name (button name) and the protocol ID is summarized. This table converts inputted protocol IDs to body part codes.

FIG. 8 shows an example of parameters for the body part such as image capturing conditions. For example, when the body part code is "100", the corresponding body part is associated with "thoracic frontal plane", and its image capturing condition with "110", its analysis function with "320", and its image processing parameter with "B10C20".

FIG. 9 shows an example of image capturing order according to embodiment 1. This order is comprised of patient information and image capturing information. Image capturing information indicates the protocol ID and protocol name of each image capturing. In this case, it is shown that images of thoracic P-A, thoracic R-L and KUB A-P are taken. "KUB" is an abbreviation for "kidney, ureter and bladder", and is an image capturing method which is classified as abdominal imaging.

Figure 10:
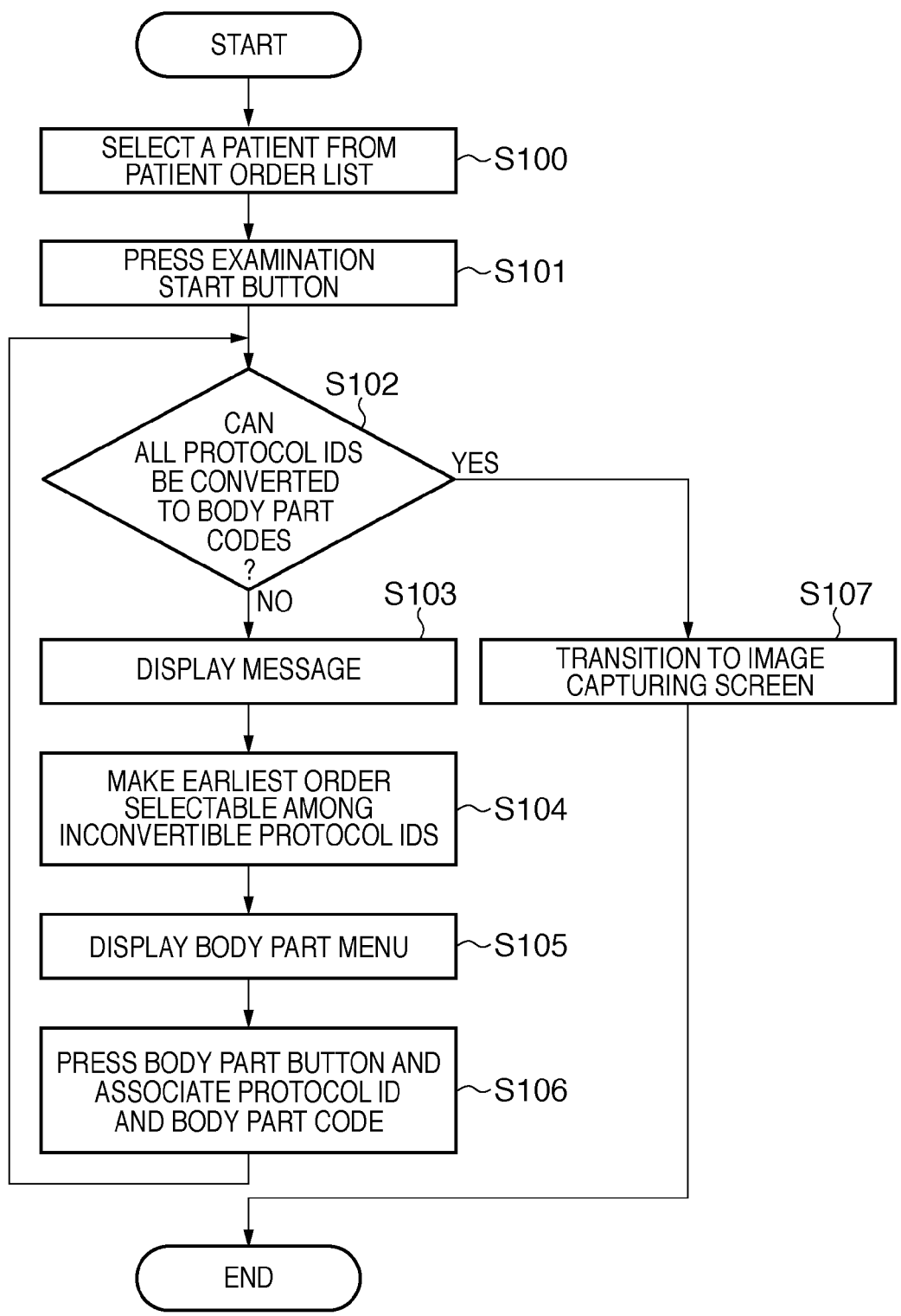
FIG. 10 is a flowchart (1) which sets undetermined protocols in embodiment 1.

FIG. 10 shows an operational flowchart according to embodiment 1 when performing association of undefined protocol IDs and body parts when the operator presses an examination start button.

Next, the present invention will be explained in further detail using FIGS. 1 to 10.

Radiologic technologists and doctors, who are the operators, determine patient information at the terminal of HIS/RIS 120. The operator selects a protocol that performs examination from the protocols shown in FIG. 5, and creates an image capturing order information such as one shown in FIG. 9. In the case of this order information, image capturing is to be performed in the order of thoracic P-A (standing), thoracic R-L (standing), and KUB A-P (standing). The image capturing order receiving unit 85 receives this image capturing order image via the network 110, and displays the image capturing order list shown in FIG. 2 on the operation display unit 89. At this time, patient information of the received image capturing order is also displayed on the image capturing order list 20.

As in step S100 of FIG. 10, when the operator selects a patient from the image capturing order list 20 whose images are to be captured, the image capturing order creating unit 88 generates image capturing information of the selected patient, and displays on the image capturing order display region 32 as shown in FIG. 2. At this time, a patient information object which summarizes patient information such as patient name, patient ID, gender, is generated. Further, in the example of FIG. 2, Hanako Suzuki who is at the top of the image capturing order list 20 is selected, and the image capturing order for the selected patient is displayed on the image capturing order display region 32.

Next, the conversion unit 86 from protocol code to body part code of FIG. 1, uses the body part conversion table 87, and converts the received protocol code to a corresponding body part. Since the first body part for Hanako Suzuki is thoracic P-A (standing), and the protocol ID is 100200120, it can be understood by referring to the body part converting table of FIG. 7 that the corresponding body part code is 100 and the body part name is "thoracic frontal". Accordingly, the image capturing order creating unit 88 displays a button that is labeled "thoracic frontal" at the top of the image capturing order display region 32. Similarly, since the body part code corresponding to the second protocol ID 100200130 is 120, and the body part name is "thoracic side", the image capturing order creating unit 88 displays a button labeled "thoracic side" in the second slot from the top of the image capturing order display region 32.

On the other hand, the body part code that corresponds to the third protocol having ID 100800110 cannot be found at the conversion unit 86 from protocol code to body part code. Therefore, as shown on the button third from the top of the image capturing order display region 32 of FIG. 2, the protocol ID is shown on the button.

The operator, upon confirming the patient information on the image capturing order display region 32, calls up the patient, and presses the image capturing start button 22 for ordering image capturing at step S101 of FIG. 10.

Subsequently, at step S102, it is checked whether all protocol IDs can be converted to body part codes.

If convertible, at step S107 the image capturing order creating unit 88 transitions to an image capturing screen like the screen shown in FIG. 4.

On the other hand, if not convertible, the image capturing order creating unit 88 at step S103 displays a message which reads, "There is a protocol ID which is not associated with a body part. Please associate the protocol ID to a body part."

At step S104, the image capturing order creating unit 88 enables selection of the unconverted protocol ID which is the earliest in order and is at the top of the list on the image capturing order display region 32. At the same time, the body part menu 23 for making association at step S105 is displayed on the operation display unit 89 as shown in FIG. 3.

Subsequently, at step S106, the operator presses the body part button from the body part menu 23, and makes an association between protocol ID and body part code. At this time the operator checks the list of protocols shown on FIG. 5 and the protocol IDs displayed on the body part buttons. And the operator determines that the KUB frontal button can be selected as the body part button.

First the operator switches the tab of the body part menu 23 of FIG. 3 to "abdominal region", and selects the KUB frontal button from the abdominal body part menu. After pressing the KUB frontal button, association of the body part selected by the undefined protocol ID assigning unit 93 and protocol ID is executed. And the temporary body part table 92 stores this association information. Along with this, the image capturing order creating unit 88 displays the associated body part instead of the button on which the protocol ID is shown. According to the operation described above, association of inconvertible protocol ID and body part is completed.

The process returns to step S102 and determines whether all protocol IDs can be converted to body part codes.

When all protocol IDs can be converted to body part codes, the image capturing order creating unit 88 at step S107 transitions to an image capturing screen shown in FIG. 4. The body part button of the image capturing order display region 32 shown in FIG. 4 indicates body part shown in FIG. 8.

When a body part is selected from the body part specifying unit 90, the image and patient/image information linking unit 82 configures various parameters such as preset image capturing conditions and image processing parameters. Also at this time, an image object which summarizes these pieces information is generated and linked to the patient object.

Next, the patient 109 is ordered to stand up as shown in FIG. 1, and positioning is performed by stepping on a pedal of a lifting unit (not shown in the figure) and moving the lifting unit vertically such that the patient 109 is at an appropriate position in relation to the image capturing unit 1003. For example, when capturing images of "Thoracic PA", the operator generally adjusts the image capturing unit 1003 such that the upper edge of the image capturing unit 1003 is level with the shoulders of the patient. Further, by moving the X-ray tube bulb 1000 back and forth, the operator performs changes in distance between the patient and the tube bulb, and makes adjustments to the irradiation field aperture such that parts other than the region being imaged are not irradiated with X-ray.

On the other hand, the image reading control unit 81 applies electric voltage to the solid-state image sensor using solid-state image sensor driving control signals, and readies the solid-state image sensor for input of images of the patient 109 at any time.

Further, the various parameters that are configured are transferred to the image capturing unit 1003 of FIG. 1, the X-ray image capturing system control unit 1006, and the X-ray generating device control unit 1001. By doing so, the X-ray image capturing system is put in a state in which it is capable of capturing images according to specified parameters. The various parameters mentioned here includes image capturing parameters, image processing parameters, correction processing parameters, generator setting parameters, etc.

Subsequently, the operator presses the X-ray irradiation button placed in close proximity to the operation display unit 89 of the X-ray image capturing device. This irradiation button is the trigger which causes the X-ray tube bulb 1000 to generate X-rays, and generates a signal to irradiate when pressed by the operator.

The irradiation signal generated by pressing the irradiation button is initially supplied to the image reading control unit 81. The image reading control unit 81 which has received this irradiation signal, checks whether the solid-state image sensor is in a state in which the received X-rays from the X-ray tube bulb 1000 can be imaged, using the status of driving notification signals generated from the solid-state image sensor. When the checking has been completed, the image reading control unit 81 generates an irradiation authorizing signal for the irradiation switch. This irradiation authorizing signal turns on the irradiation authorizing switch, and supplies the irradiation signal generated from the irradiation button to the X-ray generating device control unit 1001. In this case, the irradiation signal is generated when the second switch of the irradiation button is pressed.

The X-ray generating device control unit 1001 sends the irradiation signal to the X-ray tube bulb 1000. By doing so, X-rays are generated from the X-ray tube bulb 1000. The irradiation conditions at this time are those image capturing conditions which are configured for each individual image capturing method shown in FIG. 5. The X-ray generating device control unit 1001 irradiates X-rays for the specified time period. However, if the total sum of the X-ray amount signal taken to and accumulated at the X-ray generating device control unit 1001 via the region selected by the AEC reaches a preset amount, the X-ray generating device control unit 1001 stops the generation of X-rays at the X-ray tube bulb 1000.

On the other hand, after receiving the irradiation described above, the X-rays from the X-ray tube bulb 1000 are adjusted by an irradiation field aperture (not shown) and pass through the patient 109, the grid (not shown) and the scintillator (not shown) sequentially, and the X-rays form an image at the solid-state image sensor as a transmission image of the patient 109. Then, by the photoelectric conversion by the solid-state image sensor, the light signals are converted to image signals and outputted. Further, this analog image signal is digitalized at the A/D converter. Then, the digital signal is taken from the image reading control unit 81 and various types of correction are performed on the signal such as correction of fluctuation between photoelectric conversion elements which comprises the sensor, correction of temporal changes in the sensor element, scattered radiation correction, and image correction such as grid correction.

The image that has been imported is associated with the generated patient object and the image object by the image and patient/image information linking unit 82. Further, at the image processing section 83, various types image processing are performed on the imported image. For example, on the original image generated by the image reading control unit 81, extraction of the area of interest and exposure field, and analysis for extraction of a part of X-rays which is not captured are performed. If the image is a "thoracic frontal", regions of the lungs are extracted. And based on the extracted irradiation field region data, the images are cut out to a desired size, converted using a desired density characteristic curve, and creates images of desired tone.

As shown in FIG. 4, the created image is displayed as a captured image on the image display region 33 of the operation display unit 89. The operator, by observing the captured image, determines whether the subject is blurred, whether the graininess is at an appropriate level, and whether the posture of the subject is correct, and further checks whether contrast and density are appropriate. If they are not appropriate, the operator may repeat the image capturing, or adjust image processing parameters.

When image has been checked, the operator presses a button 38 labeled "next image" and performs the subsequent round of image capturing. At the image capturing order display region 32, the button for the thoracic frontal shot labeled "thoracic side" is selected, and performs image capturing in the same manner. Likewise, at the subsequent round of image capturing, the operator selects the button labeled "KUB frontal" which is associated to the undefined protocol ID 100800110 (KUB AP (Standing)). By selecting this button, the various types of parameters (image capturing parameters, image processing parameters, correction processing, parameters for generator setting) which are preset within the "KUB frontal" button are set, and KUB frontal image capturing is performed.

When all image capturing and image checking have been completed, the operator presses the image capturing end button 39 of FIG. 4 and ends image capturing. Then the image transferring section 84 transfers corrected images to the image server and/or printers via the network 110. Further, when the button 39 labeled "end image capturing" is pressed, the image capturing order creating unit 88 asks whether the association KUB frontal button to the unassigned protocol ID 100800110 (KUB AP (standing)) is to be registered to the body part conversion table 87. The image capturing order creating unit 88 displays a dialog for this. When the association is to be registered, the undefined protocol ID assigning unit 93 replaces the body part conversion table 87 by referring to the temporary body part table 92. In this case, the undefined ID protocol ID assigning unit 93 adds the protocol ID 100800110 to the KUB frontal protocol ID from the association table of body part and protocol of FIG. 7.

When image processing parameters are adjusted, a new body part may be added to the table by inputting a new body part title and issuing a new body part code. Further, when re-writing of the body part conversion table 87 is completed, the association information of KUB frontal button to the protocol ID 100800110 (KUB AP (standing)) of the temporary body part table 92 is deleted.

In the example described in embodiment 1, association of undefined protocol IDs to body parts is performed when the examination start button is pressed. However, the association may also be performed when the button in the image capturing order display region 32 of FIG. 4 is pressed.

Figure 11:
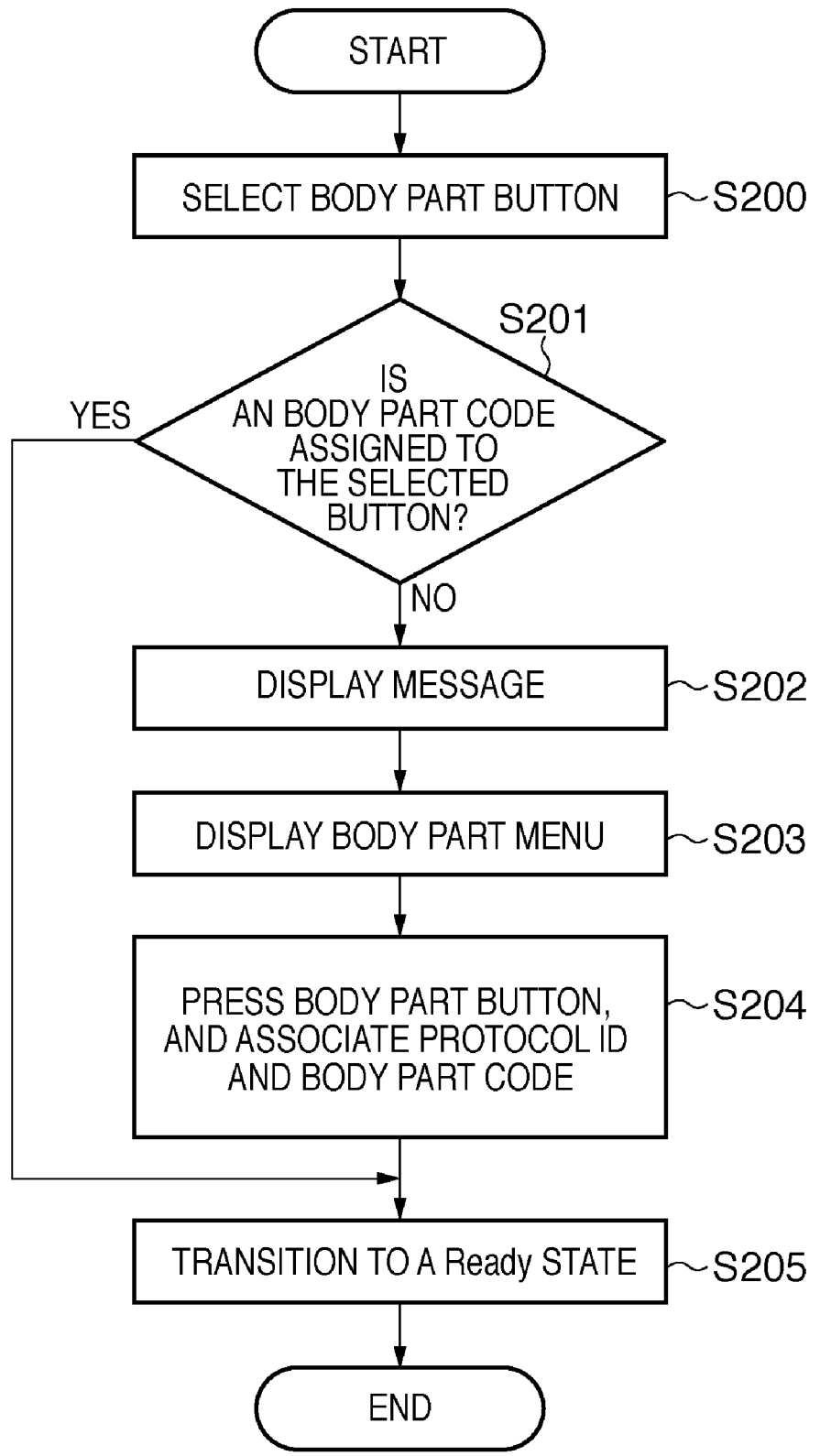
FIG. 11 shows a flowchart (2) which sets undetermined protocols in embodiment 1.

FIG. 11 shows an example of an operational flowchart for performing association of an undefined protocol ID and a body part when the button of image capturing order display region 32 is pressed.

At step S200, the operator presses the button of the image capturing order display region 32.

At step S201, the conversion unit 86 from protocol code to body part code checks whether a body part code is assigned to the selected button. If assigned, the process moves to step S205.

At step S202, if not assigned, the image capturing order creating unit 88 displays a message which reads "please select a body part".

At step S203, the image capturing order creating unit 88 displays the body part menu.

At step S204, the operator presses a body part button and makes association between protocol ID and body part code. By doing so, association of the undefined protocol ID with a body part is completed, and the system transitions to a ready state at step S205.

At this point, if a general user and a manager user are logged in, the general user may be prohibited from writing into the body part conversion table 87 at the time of image capturing completion, and allow the manager user to write. In other words, depending on authority of user who is performing image capturing, in the case of the general user, the association information of newly associated body part and image capturing condition ID is temporarily stored and destroyed afterwards. In the case of the manger user, maintainability of the system is improved by storing the association information even when the power is turned off, and has the association information incorporated into the body part conversion table 87.

As discussed above, even when an undefined protocol ID is received, image capturing according to parameters of desired body part is possible. Further, it is also possible to store the association not as an existing body part, but as a new body part.

According to the method describe above, the undefined protocol ID is displayed on top of a button in the image capturing order display region 32, the method yields an effect of making it easy for the operator to recognize the corresponding body part by looking at the protocol ID list.

Figure 12:
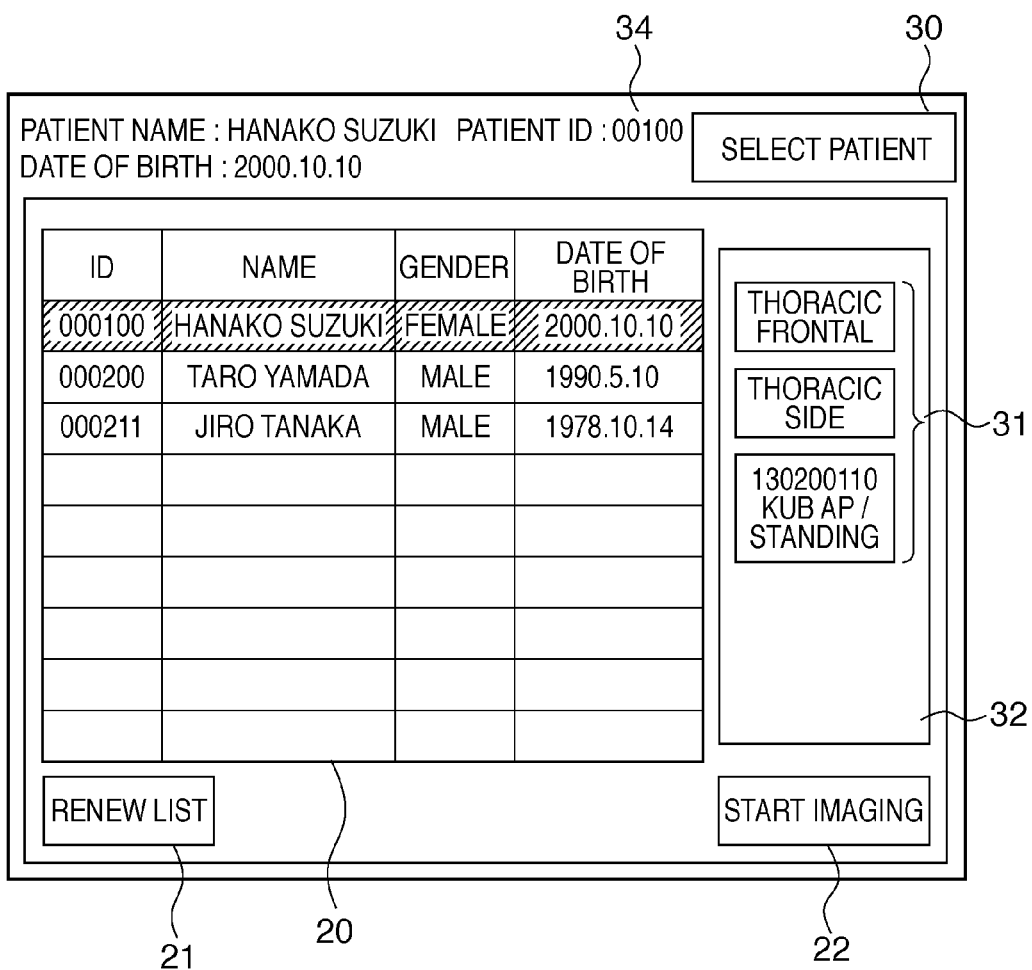
FIG. 12 shows a GUI (selection of patient) regarding display of additional image capturing information displayed on the operation display unit.
Figure 13:
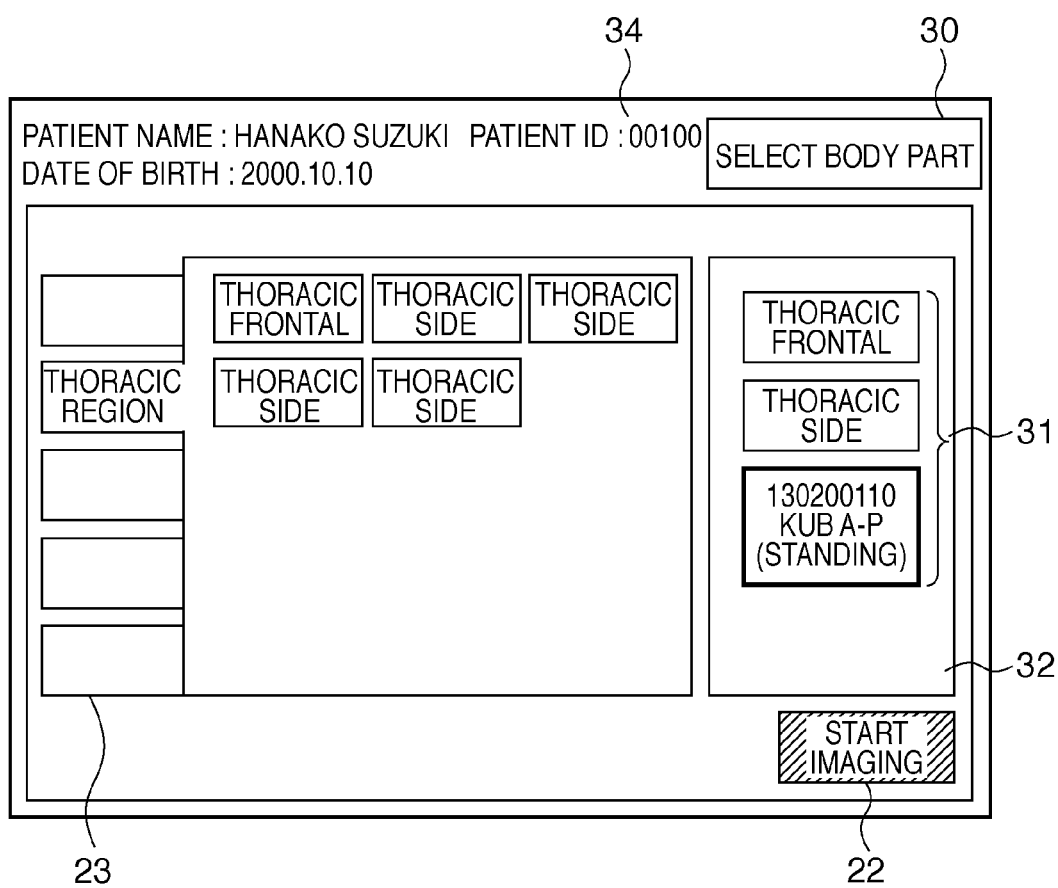
FIG. 13 shows a GUI (selection of body part) regarding display of additional image capturing information displayed on the operation display unit.

FIGS. 12 and 13 are examples of displaying related information other than undefined protocol ID, such as protocol name, on the screen for selecting a patient shown in FIG. 2, and on the screen for selecting a body part in FIG. 3. With this, the operator is able to find a desirable body part from the body part menu with greater ease.

Further, in a case as shown in FIG. 6 where the protocol ID is comprised codes that indicate examination region, posture, direction of irradiation, etc., it is possible to display its content by analyzing the codes of the protocol ID and referring to the definition file even if related information such as protocol name is not sent. The definition file for the examination region code, posture code, irradiation direction code is written into media by the RIS terminal, and the media can be read by the control unit 1006 of the X-ray image capturing system. Further, it is also possible to input definition file of the examination region code, posture code and irradiation direction code online via the network.

As described, when the definition file is obtained, the type of the region can be understood, and thus the tab of the body part menu 23 of FIG. 3 can be switched to regions shown in FIG. 6. For example, the protocol ID of KUB-PA (standing) is 130200100, it can be understood by referring to FIG. 6 that 1032 indicates abdominal, that 00 indicates standing, and that 110 indicates "PA". Therefore, it is possible to display "Abdominal Standing PA".

Embodiment 2

A method will be explained which enables the operator to associate an undefined protocol ID to a body part at times other than image capturing. Figures used to explain embodiment 2 are FIGS. 14, 15 and 16.

Figure 14:
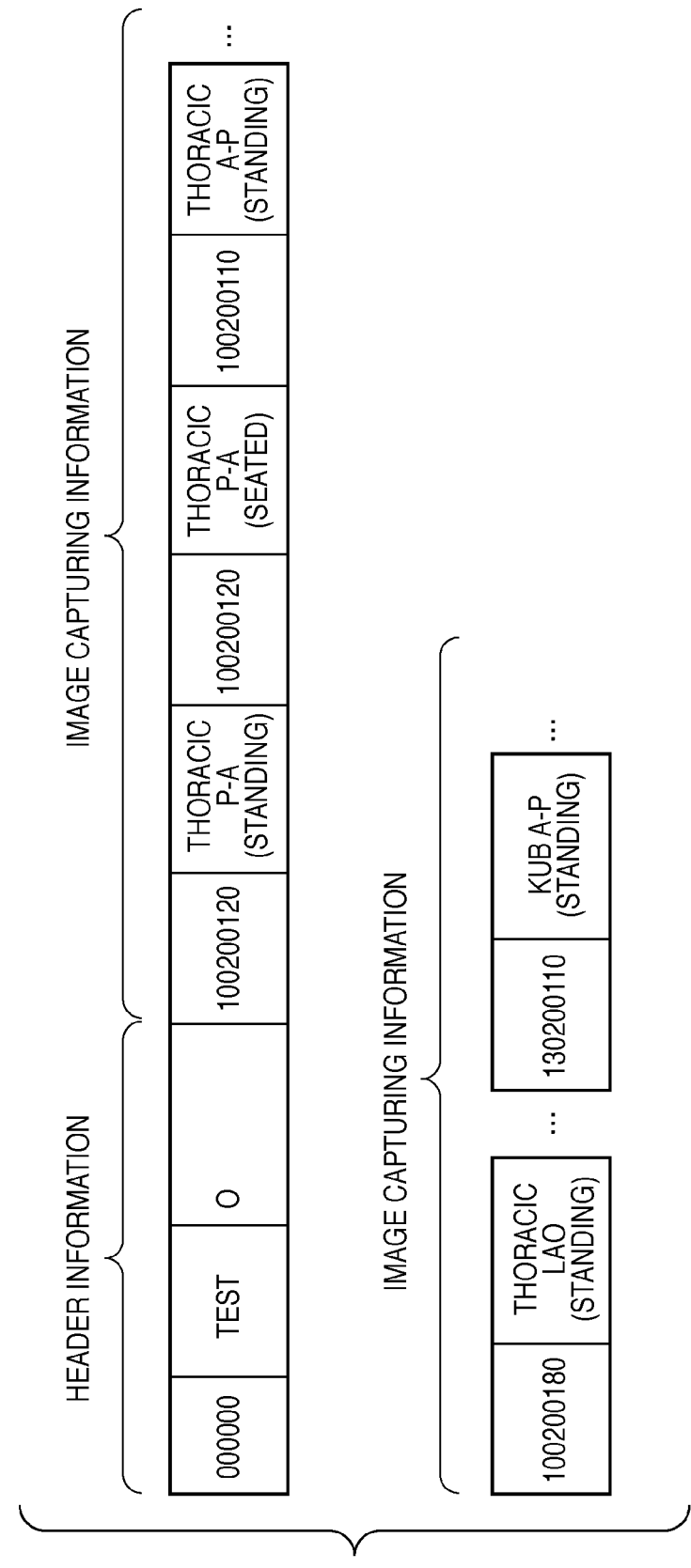
FIG. 14 shows an order which associates undetermined protocol IDs and body parts when X-ray image capturing is not taking place, according to embodiment 2.

FIG. 14 shows data for testing created by the HIS/RIS 120.

Figure 15:
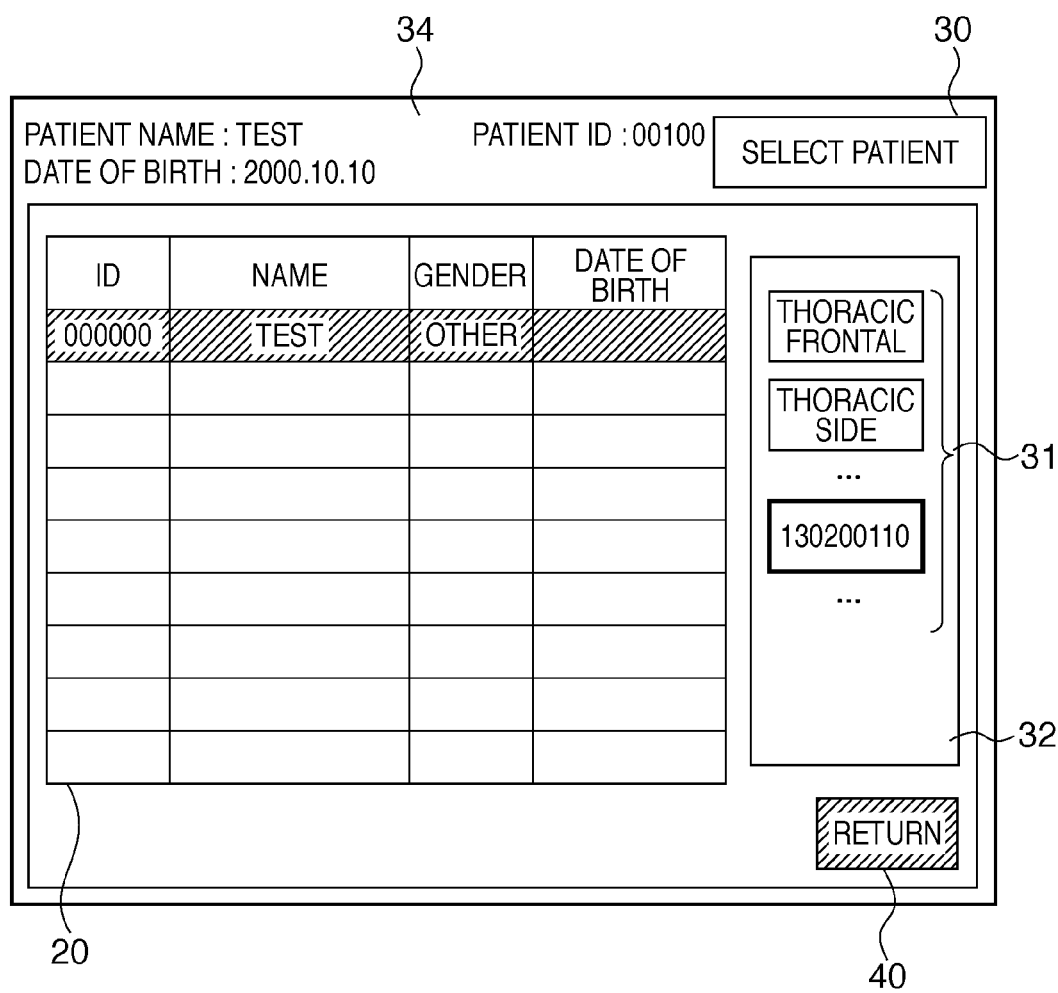
FIG. 15 shows a GUI (selection of patient) displayed on an operation display unit according to embodiment 2.

FIG. 15 is a screen for the operator to select patient according to embodiment 2.

Figure 16:
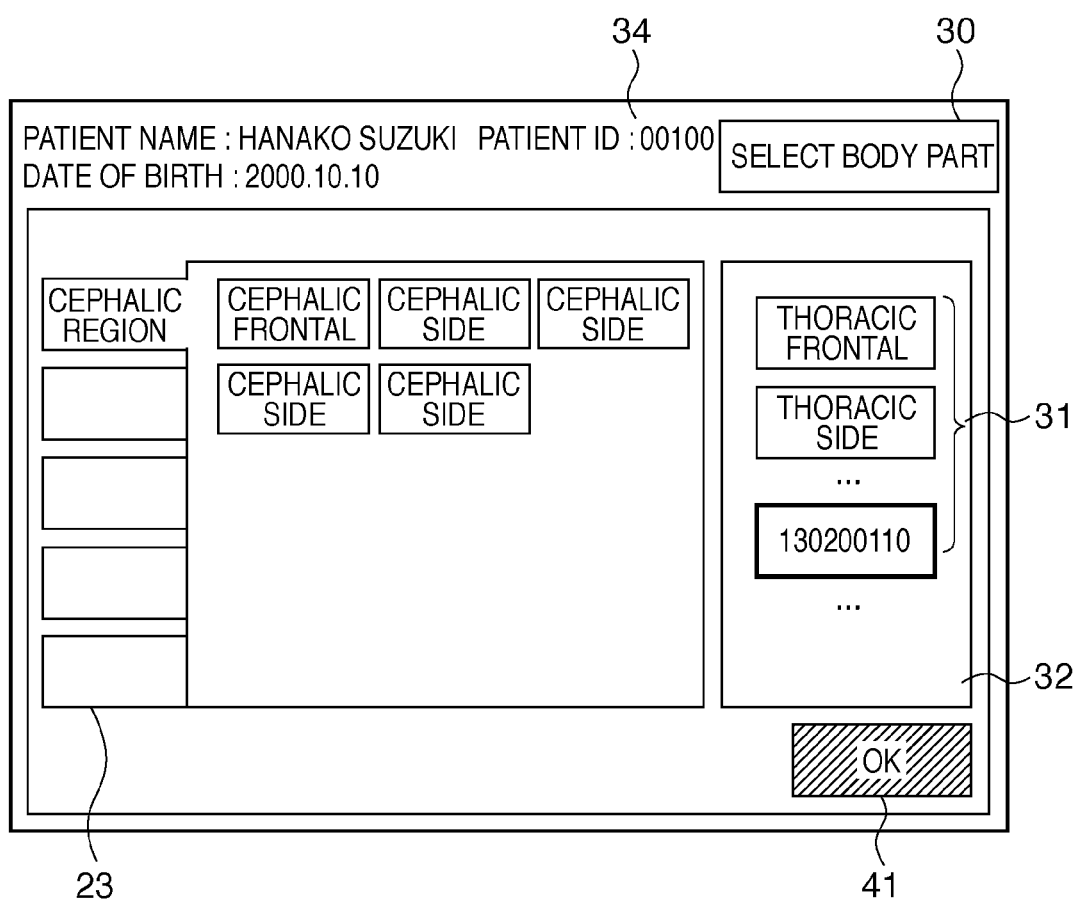
FIG. 16 shows a GUI (selection of body part) displayed on the operation display unit according to embodiment 2.

FIG. 16 is a screen for the operator to select body part according to embodiment 2.

As in embodiment 1, the image capturing order receiving unit 85 receives via the network 110 the testing data shown in FIG. 14, and displays an image capturing order list 20 shown in FIG. 15. If the operator selects the test data of the image capturing order list 20, the image capturing order creating unit 88 displays body part button sequentially on the image capturing order display region 32. If there is no corresponding body part, the protocol ID is displayed just as it was done in embodiment 1.

At this point, if the operator presses the button showing protocol ID, the image capturing order creating unit 88, as shown in FIG. 16, displays the body part menu 23 for making association. If the operator selects a body part from the body part menu 23, the image capturing order creating unit 88 displays a dialog which checks whether the association to be made is to "associate as a new body part" or to "associate to an existing body part".

If "associate as a new body part" is selected, the title of the body part and the place for the button within the image capturing menu are specified, and the selection is subsequently confirmed.

When "associate to an existing body part" is selected, association between an existing body part and the protocol ID is made. When the operator presses an OK button 41, the body part conversion table 87 stores the association information. FIGS. 15 and 16 are called up by pressing a system menu button (not shown) which is used for maintenance.

By having the configuration of embodiment 2 described above, it is possible to easily and accurately associate an undefined protocol ID a certain body part by displaying a button showing the undefined protocol ID in the image capturing order displaying region 32, even when not capturing images.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-316273, filed on Dec. 11, 2008 which is hereby incorporated by reference herein in its entirety.

What is claimed is:

1. An X-ray image capturing device comprising:
a register unit for registering at least one body part and parameters related to the image capturing the region;
a candidate display unit for displaying the body part(s) registered in said registered unit as candidates for undefined-image capturing information; and
a candidate associating unit for associating a body part selected by a user from the candidates with the undefined-image capturing information,
wherein X-ray image capturing is performed using the body part associated with the undefined-image capturing information by said candidate associating unit and the parameters related to capturing an image of the region.

2. The X-ray image capturing device according to claim 1, further comprising:
an order receiving unit for acquiring an image capturing order;
an associating unit for associating image capturing information included in the image capturing order which indicates image capturing to be performed with the body part(s) registered in said register unit; and
a display unit which displays undefined-image capturing information that could not be associated with a body part by said associating unit,
wherein X-ray image capturing is performed using the body part associated with the image capturing information by said associating unit and said candidate associating unit and the parameters related to capturing an image of the region.

3. The X-ray image capturing device according to claim 2, wherein the image capturing information included in the image capturing order comprises a code which recognizes a body part.

4. The X-ray image capturing device according to claim 2, wherein said candidate display unit displays the body part(s) of the candidates and their capturing conditions when selection of the undefined-image capturing information displayed by said display unit is received.

5. The X-ray image capturing device according to claim 2, wherein said display unit further performs display which designates image capturing when the association of the undefined-image capturing information with a body part is completed.

6. The X-ray image capturing device according to claim 3, wherein the image capturing order includes patient information and image capturing information, and is received by said order receiving unit from an information system via a network.

7. The X-ray image capturing device according to claim 2, wherein:
said register unit registers, in a nonvolatile storage medium which preserves storage even when power is turned off, body parts and their image capturing conditions in association with image capturing information such that they can be referred to by said associating unit; and
said candidate associating unit registers associations of the undefined-image capturing information with the selected body part in a temporary storage medium which preserves storage only while the power is turned on.

8. The X-ray image capturing device according to claim 7, further comprising a reflecting unit which reflect the association image capturing information and body part registered in the temporary storage medium to the nonvolatile storage medium.

9. The X-ray image capturing device according to claim 8, wherein said reflecting unit determines either to reflect, to the nonvolatile storage medium, the association of the image capturing information and the body parts registered in the temporary storage medium according to the type of authority held by the user who performed the image capturing, or to destroy the association of the image capturing information and the body part registered in the temporary storage medium.

10. The X-ray image capturing device according to claim 2, further comprising:
an image capturing unit for performing X-ray image capturing using the body part associated with the image capturing information by said associating unit and said candidate associating unit and the parameters related to capturing an image of the region.

11. A method of image capturing of X-ray image capturing device, comprising:
a step of registering at least one body part and image capturing conditions thereof;
a step of displaying the registered body parts as candidates for undefined-image capturing information;
a step of associating a body part selected by a user from the candidates with the undefined-image capturing information,
wherein X-ray image capturing is performed using the body part associated with said image capturing information in said associating step and the parameters related to capturing an image of the region.

12. A non-transitory computer-readable storage medium which stores a computer program which causes a computer to perform the image capturing method according to claim 11.

* * * * *